(12) United States Patent
Rosati

(10) Patent No.: US 7,263,814 B2
(45) Date of Patent: Sep. 4, 2007

(54) METHOD AND APPARATUS FOR SUPPLYING GAS TO AN AREA

(75) Inventor: Coni F. Rosati, Carlsbad, CA (US)

(73) Assignee: Oxyband Technologies, Inc., Mill Valley, CA (US)

( * ) Notice: Subject to any disclaimer, the term of this patent is extended or adjusted under 35 U.S.C. 154(b) by 0 days.

(21) Appl. No.: 11/183,284

(22) Filed: Jul. 15, 2005

(65) Prior Publication Data

US 2005/0251084 A1     Nov. 10, 2005

Related U.S. Application Data

(62) Division of application No. 10/781,965, filed on Feb. 18, 2004, now Pat. No. 7,014,630.

(60) Provisional application No. 60/479,745, filed on Jun. 18, 2003.

(51) Int. Cl.
*B65D 81/20* (2006.01)

(52) U.S. Cl. .................. 53/432; 53/433; 53/434; 53/400; 53/403; 53/449; 53/170; 53/173; 206/213.1

(58) Field of Classification Search .......... 53/432–434, 53/400, 403, 449, 170, 173; 206/213.1
See application file for complete search history.

(56) References Cited

U.S. PATENT DOCUMENTS

| 3,419,400 | A | 12/1968 | Hayhurst et al. |
| 3,610,238 | A | 10/1971 | Rich, Jr. |
| 3,742,951 | A | 7/1973 | Zaffaroni |
| 3,996,934 | A | 12/1976 | Zaffaroni |
| 4,003,371 | A | 1/1977 | Fischer |
| 4,055,672 | A | 10/1977 | Hirsch et al. |
| 4,201,211 | A | 5/1980 | Chandrasekaran et al. |
| 4,211,223 | A | 7/1980 | LoPiano |
| 4,224,941 | A | 9/1980 | Stivala |
| 4,236,513 | A | 12/1980 | Lopiano |

(Continued)

FOREIGN PATENT DOCUMENTS

GB      2 395 906      6/2004

(Continued)

OTHER PUBLICATIONS

*Biobased Packaging Materials for the Food Industry*, ed. Weber, C., Nov. 2002.

(Continued)

*Primary Examiner*—John Sipos
*Assistant Examiner*—Michelle Lopez
(74) *Attorney, Agent, or Firm*—Mintz, Levin, Cohn, Ferris, Glovsky and Popeo, P.C.

(57) ABSTRACT

An apparatus for supplying one or more gases, such as oxygen, to a target area, comprising a top layer and a bottom layer sealed around the perimeter of the layers to form a reservoir between the layers, wherein the top layer is not gas-permeable and the bottom layer is highly gas-permeable, said reservoir containing one or more gases. The present invention also describes methods of using such an apparatus to supply oxygen to a wound for improved wound healing.

4 Claims, 6 Drawing Sheets

U.S. PATENT DOCUMENTS

| | | |
|---|---|---|
| 4,296,743 A | 10/1981 | Lasley |
| 4,328,799 A | 5/1982 | LoPiano |
| 4,432,354 A | 2/1984 | Lasley |
| 4,460,368 A | 7/1984 | Allison et al. |
| 4,474,571 A | 10/1984 | Lasley |
| 4,497,406 A | 2/1985 | Takanashi |
| 4,624,656 A | 11/1986 | Clark et al. |
| 4,747,841 A | 5/1988 | Kuratomi et al. |
| 4,779,398 A | 10/1988 | Glandon et al. |
| 4,801,291 A | 1/1989 | Loori |
| 4,813,210 A * | 3/1989 | Masuda et al. ............... 53/434 |
| 4,839,345 A | 6/1989 | Doi et al. |
| 4,842,875 A | 6/1989 | Anderson |
| 4,875,483 A | 10/1989 | Vollmann et al. |
| 4,895,729 A | 1/1990 | Powrie et al. |
| 4,906,463 A | 3/1990 | Cleary et al. |
| 4,919,955 A | 4/1990 | Mitchell |
| 4,969,881 A | 11/1990 | Viesturs |
| 5,008,110 A | 4/1991 | Benecke et al. |
| 5,014,494 A * | 5/1991 | George ........................ 53/432 |
| 5,029,579 A | 7/1991 | Trammell |
| 5,154,697 A | 10/1992 | Loori |
| 5,308,887 A | 5/1994 | Ko et al. |
| 5,336,209 A | 8/1994 | Porzilli |
| 5,354,569 A * | 10/1994 | Brown et al. ............... 426/411 |
| 5,354,790 A | 10/1994 | Keusch et al. |
| 5,478,310 A | 12/1995 | Dyson-Cantwell et al. |
| 5,481,852 A | 1/1996 | Mitchell |
| 5,487,889 A | 1/1996 | Eckert et al. |
| 5,578,022 A | 11/1996 | Scherson et al. |
| 5,583,114 A | 12/1996 | Barrows et al. |
| 5,662,625 A | 9/1997 | Westwood |
| 5,707,499 A | 1/1998 | Joshi et al. |
| 5,788,682 A | 8/1998 | Maget |
| 5,792,090 A | 8/1998 | Ladin |
| 5,855,570 A | 1/1999 | Scherson et al. |
| 5,865,722 A | 2/1999 | Heng |
| 5,901,848 A | 5/1999 | Gorlich et al. |
| 5,916,615 A | 6/1999 | Brady et al. |
| 5,948,457 A | 9/1999 | DelDuca et al. |
| 6,000,403 A | 12/1999 | Cantwell |
| 6,210,725 B1 | 4/2001 | Colombo |
| 6,248,380 B1 | 6/2001 | Kocher et al. |
| 6,256,905 B1 | 7/2001 | White |
| 6,284,941 B1 | 9/2001 | Cox et al. |
| 6,342,261 B1 | 1/2002 | Spencer |
| 6,432,077 B1 | 8/2002 | Stenzler |
| 6,458,109 B1 | 10/2002 | Henley et al. |
| 6,465,708 B1 | 10/2002 | Augustine et al. |
| 6,465,709 B1 | 10/2002 | Sun et al. |
| 6,471,685 B1 | 10/2002 | Johnson |
| 6,481,185 B1 | 11/2002 | Buchko |
| 6,548,132 B1 | 4/2003 | Clarke et al. |
| 6,572,594 B2 | 6/2003 | Satterfield et al. |
| 6,767,342 B1 | 7/2004 | Cantwell |
| 6,816,536 B2 | 11/2004 | Julliard et al. |
| 6,877,601 B1 * | 4/2005 | Colombo ................ 206/213.1 |
| 6,996,952 B2 * | 2/2006 | Gupta et al. ................. 53/434 |
| 2001/0020146 A1 | 9/2001 | Satterfield et al. |
| 2003/0190367 A1 | 10/2003 | Balding |
| 2004/0116770 A1 | 6/2004 | O'Connor et al. |
| 2005/0112245 A1 | 5/2005 | DelDuca et al. |

FOREIGN PATENT DOCUMENTS

| | | |
|---|---|---|
| WO | WO 03/003989 | 1/2003 |
| WO | WO 03/049660 | 6/2003 |

OTHER PUBLICATIONS

Brody, A. (2001). *Food Technology 55*: 104-106, What's Active in Active Packaging.

Devlieghere et al. "Modified atmosphere packaging: state of the art", Sep. 2000, http://www.ifis.co.uk/hottopics/MAParticle2.pdf, *Modified Atmosphere Packaging: State of the Art*.

Eaglstein, W. (1985). *J. AmM. Acad. Dermatol. 12*: 434-440, Experiences with Biosynthetic Dressings.

Fischer, B. (1975). *J. of Derm. Surg. 1*: 55-58, Treatment of Ulcers on the Legs with Hyperbaric Oxygen.

Gruber et al. (1970). *Arch. Surg. 101*: 69-70, Skin Permeability to Oxygen and Hyperbaric Oxygen.

Heng et al. (1984). *Arch. Dermatol 120*: 640-645, A Simplified Hyperbaric Oxygen Technique for Leg Ulcers.

Hoogerwerf et al. (2002). *Letters in Applied Microbiology 35*: 419-422, A Simplified Hyperbaric Oxygen Technique for Leg Ulcers.

Kaufman et al. (1983). *Burns 9*: 169-173, Topical Oxygen and Burn Wood Wound Healing: a Review.

Kaufman, et al., Proceedings of the 39th Annual Sessions of the Forum on Fundamental Surgical Problems, 69th Clinical Congress, American College of Surgeons, Atlanta, GA, Oct. 1983, pp. 109-113, *Acceleration of Wound Healing and Contraction of Experimental Deep Burns by Topical Oxygen*.

Labell, F. (1985). *Food Processing* January, 152-154, Controlled & Modified Atmospheric Packaging.

Niinikoski, J. (1977). *Clinics in Plastic Surgery 4*: 361-374, Oxygen and Wound Healing.

Niinikoski and Allan (1983). *Infections in Surgery* 23-37, Combination of Hyperbaric Oxygen, Surgery and Antibiotics in the Treatment of Clostridial as Gangrene.

Olejniczak and Zielinski (1976). *Medical Times 104*: 114-121, Topical Oxygen Promotes Healing of Leg Ulcers.

Prockop et al. (1963). *Arch. Biochem. & BioPhys, 101*: 499-503, Oxygen-18 Studies on the Conversion of Proline to Collagen Hydroxyproline.

Silver, I. (1972). In *Epidermal Wound Healing*, ed. Maibach, H. and Rovee, D., Year Book Medical Publishers, Inc. Chicago, pp. 291-305, Oxygen Tension and Epithelialization.

Silver, I. (1980). In *Wound Healing & Wound Infection*, ed. Hunt, T.K., Appleton-Century-Crofts, NY, pp. 11-31, The Physiology of Wound Healing.

Transcript of the U.S. FDA, Center for Drug Evaluation & Research, Dermatologic and Ophthalmic Drugs Advisory Committee, 46th Meeting, Jul. 14, 1997, pp. 15-28.

Utkina, O. (1964). *Biological Abstracts 45*: 6289, Abstract No. 78585.

Whitney, J. (1989). *Heart & Lung 18*: 466-476, Physiological Effects of Tissue Oxyenation on Wounds.

Winter, G. (1977). *Advances in Exp. Med. And Bio. 94*: 673-678, Advances in Exp. Medicine and Bio.

Winter and Perrins (1970). Proceedings of the 4th Int. Congress on Hyperbaric Medicine, Igaku Shion Ltd, pp. 363-368.

Zhao et al. (1994). *Arch. Surg. 129*: 1043-1049, Effect of Hyperbaric Oxygen and Growth Factors on Rabbit Ear Ischemic Ulcers.

* cited by examiner

METHOD AND APPARATUS FOR SUPPLYING GAS TO AN AREA

This application is a divisional of U.S. application Ser. No. 10/781,965, filed Feb. 18, 2004 now U.S. Pat. No. 7,014,630, which claims the benefit of U.S. application Ser. No. 60/479,745, filed on Jun. 18, 2003, each disclosure of which is herein incorporated by reference in its entirety.

FIELD OF THE INVENTION

The present invention relates generally to supplying a gas to an area.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

The healing of wounds and the effect of oxygen tension has been intensively studied (1). Among the components important in the healing process are fibroblast proliferation, angiogenesis, collagen synthesis, and reepithelialization.

Soon after injury, whether accidental or surgically induced, undifferentiated mesenchymal cells transform to migratory fibroblasts, which migrate into and across the injured wound. It is known that fibroblasts are aerobic in nature. Fibroblasts are stimulated to produce collagen. While experiments from cultured fibroblasts suggest that high lactate and ascorbic acid concentration typical of hypoxic conditions may activate some of the fibroblast collagen-synthesizing enzymes, animal studies involving low, normal, and high oxygen tensions nevertheless demonstrate increased rates of collagen synthesis under hyperoxic rather than hypoxic conditions.

Angiogenesis, on the other hand, appears to be stimulated by a hypoxic tissue gradient, with new capillaries extending in the direction of lower oxygen concentration. When a hypoxic gradient no longer exists, angiogenesis is minimized or static. Epithelialization is also known to be related to oxygen tension, with higher rates of epithelial proliferation observed under hyperoxic as opposed to hypoxic conditions.

The supply of oxygen to healing wound tissue may be derived from three sources: oxygen chemically bound to hemoglobin in whole blood; oxygen dissolved in plasma; and oxygen which diffuses into plasma or tissue from the exterior. In deep wounds, the latter is of little importance. The studies of R. P. Gruber et al., for example, indicate that oxygen tension, measured polarographically, increases markedly at 3 bar of 100% $O_2$ in the superficial dermis (0.30–0.34 mm), while the relative oxygen concentration of the deep dermis (1.8–2.2 mm) is unchanged under the same conditions (2).

In surface wounds, all sources of oxygen are important. In wounds of large surface area, however, for example ulcers, only the tissue at the edges of the ulcer or at its base are well supplied with blood, and the growing granulation tissue, in the absence of oxygen diffusing from the exterior, must be supplied by diffusion from blood vessels and plasma, a relatively inefficient process.

It is well established, also, that occlusive coverings that maintain a moist environment promote wound healing (3). Furthermore, it is well known that the changing of wound dressings may interfere with the healing process by disrupting the healing tissue where granulation and collagen synthesis has not imparted sufficient tensile strength to avoid rupture upon dressing removal. However, due to the inability of the blood and plasma to supply optimal oxygen concentration, and due to the further reduction in oxygen from the exterior brought about by the presence of the occluding dressing, a hypoxic condition may rapidly be reached. Although this condition may encourage angiogenesis, it negatively affects collagen synthesis and epithelialization. Moreover, various clostridium species, e.g., *C. perfringens* and *C. septicum*, are induced to germinate under hypoxic conditions, which can also support other anaerobic flora (4). In addition to minimizing anaerobic flora by discouraging germination, hyperoxic conditions are known to reduce the concentration of other pathogens as well.

Past treatment of chronic ulcers and gangrenous tissue has, in many cases, involved extensive debridement in combination with antibiotics and systemic hyperbaric oxygen. Room size hyperbaric oxygen chambers or chambers sized for the individual patient have employed pure oxygen at pressures of 2 to 3 bar. Treatment time is limited, as oxygen toxicity and central nervous system (CNS) disorders may result from the increased oxygen content of the blood. Such treatments have met with a great deal of success, but the success may not be due to the increased systemic blood and plasma-derived oxygen supply. The blood and plasma already contain sufficient oxygen for the healing process. Rather, it is the diffusion-limited access of oxygen to the wound that limits the oxygen supply required for optimal healing and minimization of infection. The increased oxygen tension in the wound most likely results directly from increased diffusion into the wound surface from the oxygen in the chamber. Gruber, for example, indicates that rate of oxygen absorption from the skin is roughly proportional to oxygen concentration from nearly 0% to 30% (2). Gruber further indicates, however, that oxygen absorption tends to level off at higher oxygen concentrations.

Due to the expense of large hyperbaric chambers and the systemic effects of oxygen toxicity that they may engender, topical hyperbaric chambers have been proposed. Topical chambers operating at "normal" hyperbaric pressures of 2–3 bar are difficult to seal to the body or extremity being treated, however, without interfering with blood supply to the wound locus. Thus, hyperbaric chambers operating at only modestly elevated pressure have been manufactured, such as a device operating at 22 mm Hg pure oxygen (1.03 bar) (5). However, such chambers are expensive and difficult to sterilize (6). Cross-infection is stated to be common.

Heng and others have proposed a simple hyperbaric oxygen treatment chamber consisting of a polyethylene bag that may be secured to the body or extremity with adhesive tape (6), or a transparent nylon bag with straps and VEL-CRO® closures (7). Pressure is maintained at between 20 mm Hg and 30 mm Hg. However, the leakage associated with the sealing of such bags requires a relatively high rate of oxygen flow. Thus, this method is useful only in facilities with sufficient oxygen supply, or in controlled home environments where a large oxygen tank is permissible. A disposable hyperbaric treatment bag with improved closure is disclosed in U.S. Pat. No. 5,029,579. Another disposable hyperbaric treatment bag is disclosed in U.S. Pat. No. 5,478,310.

In U.S. Pat. No. 4,875,483, a combination layered dressing having an external low oxygen-permeability layer and an abutting internal oxygen permeable layer has been proposed. The relatively low permeability exterior layer is left attached for 3 to 72 hours creating hypoxia, and hopefully stimulating angiogenesis, following which this layer is removed. However, although the remaining, and now exterior layer is oxygen permeable, the layer nevertheless decreases oxygen transport, and thus hyperbaric treatment, by one of the methods previously described, may be necessary to elevate oxygen levels sufficiently to provide optimal healing.

Ischemia compromises wound healing and wounds in aging populations are more ischemic than those in younger populations (8). It has been demonstrated in ischemic rabbit ear models that topical or hyperbaric oxygen can convert a non-healing wound into a healing wound, and that growth factors (PDGF) provide a synergistic benefit when used with oxygen (9).

It is well known that the speed of epidermal migration on the normal wound is critically dependent on the amount of oxygen available, and this is the rate-limiting step. The control of the local environment is dependent on the local blood supply and the diffusion of oxygen from the atmosphere. Any form of treatment that encourages an increase in the wound fluid and reduces the time during which the wound is non-perfused will tend to increase the rate of healing (10, 11).

It is generally agreed that the tissue surrounding a wound does not alone supply sufficient oxygen for wound repair, and that atmospheric oxygen is required for the formation of hydroxyproline, a key element in epidermal wound healing. It has been demonstrated that 93% of the oxygen incorporated into the hydroxyl groups of newly synthesized hydroxyproline is derived from the atmosphere (12).

It is further generally known that it is likely that oxygen reaches the epidermal cells directly by diffusion through the scab rather than via the vascular or tissue supply. Prior studies of wounds covered with plastic films found that the higher the oxygen permeability of the film, the greater the healing rate (13, 14). Furthermore, the films prevented scab formation, thereby altering the mode of epidermal regeneration. The use of wound dressings that prevent scab formation and have increased oxygen permeability are thought to improve wound healing. The increased presence of oxygen speeds the re-establishment of epithelial continuity. Direct access of pure oxygen to open wounds promotes epidermal cell migration.

Kaufman et al. showed a continuum in wound healing improvement when changing humidified oxygen levels from 21 to 60, and 80–96% on full thickness burns on guinea pigs (15). Niinikoski also suggested that collagen accumulation in the dead space of animal wounds increases with oxygen concentration of the environment, peaking at 70% (16).

A review of topical oxygen and burn wound healing states that oxygen is essential for the contraction, the dominant healing process (17). Topical oxygen has also been shown to improve the healing rate of skin ulcers and wounds where an inadequate supply of oxygen results from peripheral vascular disease or local injury to the microcirculation. Fischer showed topical hyperbaric oxygen treatment improved epithelialization and contraction of decubitus ulcers (5).

Utkina demonstrated that moderate increases in oxygen levels at normal atmospheric pressure increases the closure rate of open wounds (18). He showed healing rate improved with continuous exposure to 45%.

A number of patents have been issued that disclose the use of local generation of oxygen at the wound site to treat wounds in bandage systems using chemical reactions, oxygen saturated solutions, or electrochemical generators (see U.S. Pat. Nos. 5,855,570, 5,578,022, 5,788,682, 5,792,090 and 6,000,403). These concepts have not been commercialized. The present invention allows for gas to be contained simply into the wound dressing, which creates a wound environment with continuous exposure to preset oxygen levels, without need for a gas source such as a generator, saturated solution or a chemical reaction. Since the amount of oxygen consumed by metabolic processes in the wound is relatively small, the materials for the dressing and the volume of the oxygen cavity in the dressing can be selected to maintain the desired oxygen concentration for the practical life of the dressing.

Prior to this invention, larger amounts of oxygen were believed to be required to benefit wound healing, which justified the need for an oxygen releasing source However, the actual amount of oxygen that the wound consumes in cell metabolism is quite small, and simply requires a design that assures a large diffusion gradient for oxygen into the wound during the healing period. Hyperbaric approaches that use elevated pressure to further enhance the oxygen diffusion gradients to transfer more oxygen into the tissue are only used briefly, and once the patient is withdrawn from the high-pressure environment, the oxygen levels in the wound drop down to pre-exposure limits quickly. The present invention operates as a hyperoxic environment without the need for using elevated pressure to create the oxygen diffusion gradient.

Supplying oxygen to a wound on a continuous and ambulatory basis is of benefit to speed healing and reduce infection. The oxygen dressing described below can be complimentary to other therapies and can address a rate-limiting step for various types of wounds.

SUMMARY OF THE INVENTION

The present invention is an apparatus that is capable of providing one or more gases to a target area. One embodiment of the invention is a multi-layer wound dressing comes pre-filled with high levels of oxygen between the layers. The top layer is a barrier film that holds the oxygen over the wound, while the bottom layer is a high transfer rate film, attached over the wound. This self-contained dressing is applied to the wound like conventional wound dressings, and can be manufactured with a similar size, weight and feel of conventional dressings or transdermal patches.

The barrier layer holds the oxygen in the vicinity of the wound, while the permeable or porous layer allows the oxygen to diffuse into the wound fluid at a rate proportional the gradient, until the wound fluid is saturated. The dressing acts like an oxygen reservoir, and as oxygen is consumed by the wound, there is a local abundant supply to be used as needed.

While oxygen is a rate-limiting component in the wound healing process, the oxygen transfer across intact skin is insignificant, and oxygen consumption by a wound is a relatively small number, estimated to be $10^{-4}$ cc/mL fluid-hr. Therefore the design of the dressing is influenced most significantly by the diffusion rates of the relevant gases through the barrier material, the target gas concentration range on the patient, the length of time the dressing may be worn, and the seal integrity of the dressing to itself and to the patient.

The dressing would be removed by the user from a package that uses controlled atmospheric packaging (CAP) to maintain the product integrity. CAP is specifically a package with high barrier properties that contains the desired ratio of gases to preserve the product. CAP is well known in the food industry and examples of the types of CAP that may be used are described in U.S. Pat. No. 4,895,729 and in the published literature (19, 20, 21, 22, 23).

The dressing will accelerate healing of acute and chronic wounds, as well as provide antibacterial and antifungal benefits.

BRIEF DESCRIPTION OF THE DRAWINGS

The accompanying drawings, which are incorporated in and constitute a part of this specification, illustrate one embodiment of the invention and, together with the description, explain one embodiment of the invention. In the drawings.

DETAILED DESCRIPTION

The following detailed description of the invention refers to the accompanying drawings. The detailed description merely provides exemplary embodiment of the invention and is not intended to limit the invention.

Figure 1:
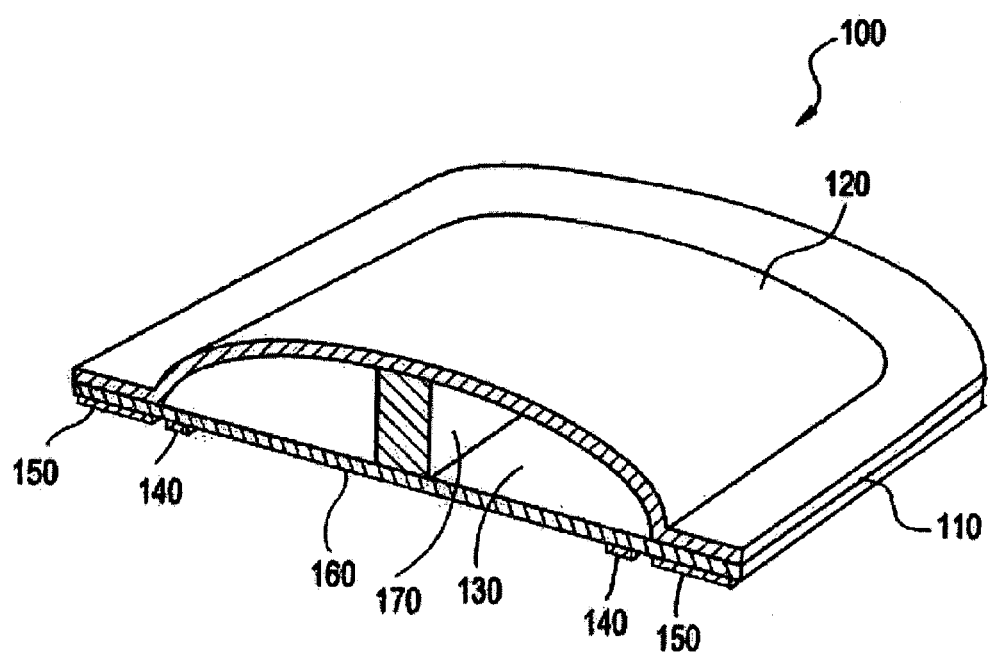
FIG. 1 illustrates one embodiment of a dressing system.

FIG. 1 illustrates an apparatus for supplying one or more gases, also referred to herein as a dressing system 100. The dressing system 100 is shown as an exemplary perspective cut-away view to more clearly illustrate the invention. In one embodiment, the dressing system 100 is configured to contain a gas that is dispensed to a user wearing the dressing system 100. For example, the different gases contained within the dressing system 100 may include but is not limited to oxygen, carbon dioxide, and/or nitrogen.

As used herein, the term "gas" includes any gas or volatile.

The dressing system 100 includes a seal 110, an external barrier (or top layer) 120, a reservoir 130, an absorbent ring 140, an adhesive backing 150, a permeable film (or bottom layer) 160, and a compliant porous insert 170.

The seal 110 is configured to bond the external barrier 120 and the permeable film 160 together such that the reservoir 130 is formed.

The external barrier 120 is selected to be non-permeable to gases. For example, the external barrier 120 may be constructed of metallized polyester, ceramic coated polyester, polyvinylidene chloride laminates such as Saranex®, EVOH laminates such as Oxyshield®, or polyamide laminates such as Capran®. In one embodiment, the external barrier 120 may be configured to conduct heat or electrical stimulation from an external source to the user. For example, polyethylene or another infrared transmittable material may be utilized as the external barrier 120.

The permeable film 160 is configured to be permeable to gases. For example, the permeable film 160 may be constructed of polyurethane, silicone, polyvinylchloride, polyolefins, and the like, preferably ethylene vinyl alcohol (EVA) or EVA/polyethylene.

The reservoir 130 is configured to store a gas while the dressing system 100 is worn by a user. In one embodiment, the stored gas within the reservoir 130 is controllably released to the user through the permeable film 160.

The amount of gas released to the user while wearing the dressing system 100 may vary according to the concentration of the gas contained within the reservoir 130 and the material used as the permeable film 160. Other factors such as temperature and atmospheric pressure may also affect the amount of gas released to the user.

The absorbent ring 140 may be located adjacent to the permeable film 160 and may be configured to wick away moisture from the user.

The adhesive backing 150 is configured to adhere the dressing system 100 to the user. Further, the adhesive backing 150 may also be utilized to prevent the gas that is delivered through the permeable film 160 to the user from escaping. In one embodiment, the adhesive backing 150 may cover the perimeter of the dressing system 100. In another embodiment, the adhesive backing may cover the entire dressing system 100 and may be integrated with the permeable film 160.

Examples of the types of adhesive that may be used in the present invention are described in U.S. Pat. Nos. 6,284,941 and 5,308,887. In one embodiment, the adhesive backing may be comprised of adhesive used in commercially available adhesive bandages. In another embodiment, the adhesive backing may be comprised of a gel adhesive. The gel adhesive may be comprised of a hydrogel. The gel adhesive may also be reusable, such that the dressing system could be removed from the user and replaced more than once.

The compliant porous insert 170 is configured to prevent gas debt in areas caused by pressing the external barrier 120 directly on to the permeable film 160. In one embodiment, the compliant porous insert 170 placed within the reservoir 130 and between the external barrier 120 and the permeable film 160.

The elements comprising the dressing system 100 are shown for illustrative purposes only. Deletion or substitution of any shown elements does not depart from the spirit and scope of the invention. Similarly, the addition of new elements does not depart from the spirit and scope of the invention.

In one embodiment, the dressing system 100 is configured to be pre-filled with high levels of oxygen within the reservoir 130. In this embodiment, the dressing system 100 is configured to be placed over a wound of the user to help the wound heal. In one embodiment, the external barrier 120 is configured to hold the oxygen within the dressing system 100 and the permeable film 160 is a high transfer rate film and is configured to provide oxygen over the wound. In other words, the external barrier 120 holds the oxygen in the vicinity of the wound, while the permeable film 160 allows the oxygen to diffuse into the wound fluid at a rate proportional the gradient, until the wound fluid is saturated.

Subsequent to the saturation, the dressing system 100 acts as an oxygen reservoir; as oxygen is consumed by the wound, there is a local abundant supply of oxygen to be provided to the wound as needed.

The proportions of the dressing system 100 may be influenced by the diffusion rates of the relevant gases through the permeable film 160, the target gas concentration range on the user, the length of time the dressing system 100 may be worn, and the seal integrity between the dressing system 100 and the user. The dressing system 100 may accelerate healing acute and chronic wounds, as well as provide antibacterial and antifungal benefits.

In another embodiment, in addition to providing gas to a user, the dressing system 100 may be configured to deliver biologically beneficial agents such as drugs, minerals, nutrition, amino acids, pH modifiers, anti-microbials, growth factors, enzymes to the user. In one embodiment, integrating the delivery systems of the gas with the beneficial agent additives may lead to synergistic effects that are not achieved by just the gas or the beneficial agent additives alone. In one embodiment, these biologically beneficial agents may be delivered as microencapsulated agents incorporated in the adhesive backing 150. In another embodiment, the microencapsulated agents may be available in a gel matrix in the reservoir 130, accessible to the wound through the pores or perforations of the permeable film 160, or using conventional transdermal technologies.

In an alternate embodiment, instead of filling the reservoir 130 with gas, a substance is included within the reservoir 130 to generate gas within the reservoir 130. For example, oxygen-releasing agents may be included within the reservoir 130. Oxygen releasing agents include oxygen releasing inorganic salts, hydrogen peroxide containing formulations, intercalated magnesium peroxide, sodium percarbonate, sodium carbonate and hydrogen peroxide, and the like.

In yet another embodiment, the permeable film 160 may be deleted and the compliant porous insert 170 may be utilized to hold a substance for generating a gas within the dressing system 100.

In yet another embodiment, the external barrier 120 is comprised of Saranex®, the permeable film 160 is a polyurethane high oxygen permeability film, these two layers are hermetically sealed around the perimeter, and the reservoir 130 contains 98% oxygen. One method of achieving the specified oxygen concentration in the reservoir 130 and to create the controlled atmospheric packaging is to (1) assemble dressing, sealing the reservoir with normal atmospheric conditions (about 21% oxygen); (2) place the dressing in the metallized film package; (3) flush the package with 100% oxygen; and (4) seal the package. In storage, the gas in the reservoir 130 will come to equilibrium with the gas in the package via the permeable film 160. When the product is received by the customer and opened, the gas in the reservoir will achieve 98% oxygen. The materials and dimensions used are determined by taking into account these objectives.

In another embodiment, the dressing system as described herein may further comprise a septum, which is defined herein as a septum, a valve, a Luer-type fitting or any resealable opening through which one or more gases can be introduced into the dressing system, then resealed to prevent the one or more gases from escaping. The dressing system of this embodiment may be applied to the wound, then the one or more gases in the desired ratio may be introduced into the dressing system, e.g., with a syringe. The septum would also allow for refilling of the dressing system, if desired.

Figure 2:
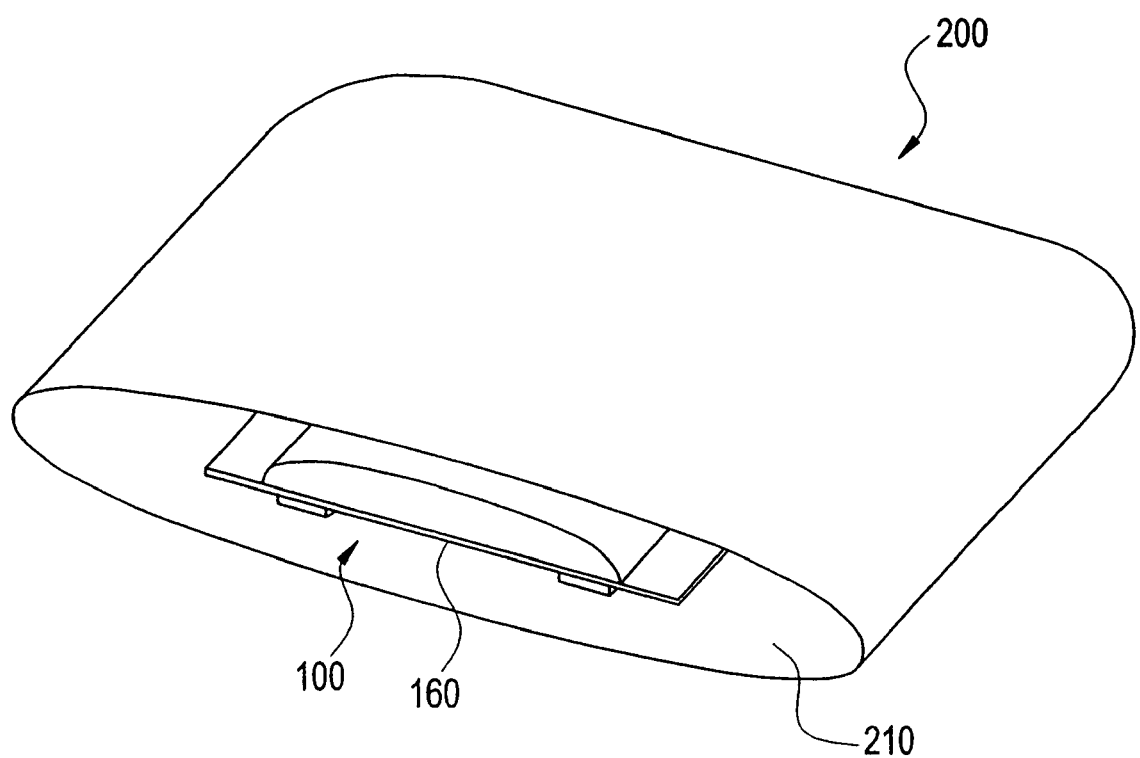
FIG. 2 illustrates one embodiment of a packaging system.

FIG. 2 illustrates a packaging system 100. The packaging system 100 is shown as an exemplary perspective cut-away view to more clearly illustrate the invention. In one embodiment, the packaging system 200 is configured to contain a gas within an enclosed container 210, which is within the packaging system. For example, the different gases contained within the dressing system 100 may include but is not limited to oxygen, carbon dioxide, and/or nitrogen.

The enclosed container 210 is also configured to hold the dressing system 100 as shown and described corresponding to FIG. 1. Once the enclosed container 210 is sealed, the enclosed container is substantially impermeable; the gas within the enclosed container 210 substantially remains within the enclosed container 210. Further, the enclosed container 210 utilizes controlled atmospheric packaging (CAP) to maintain the environment within the enclosed container 210. In one embodiment, CAP is a package with high barrier properties that contains the desired ratio of gases to preserve the internal environment.

The gas within the enclosed container 210 may permeate the dressing system 100 through the permeable film 160.

In one embodiment, the packaging system 200 may be utilized to store the dressing system 100 without degrading the gas stored within the reservoir 130 within the dressing system 100 when the gas within the reservoir 130 and the gas within the enclosed container 210 are the same.

In another embodiment, the packaging system 200 may be utilized to change the concentrations of gases in the dressing system 100. The gas constituents stored within the enclosed container 210, diffuse into the dressing system 100 when the concentration of the gas within the container 210 is higher in concentration compared to the gas within the dressing system 100. Similarly, the gas constituents stored within the dressing system 100, diffuse into the container 210 when the concentration of the gas within the container 210 is lower in concentration compared to the gas within the dressing system 100. The gases may diffuse through the permeable film 160 until the constituents reach equilibrium, the same concentrations on both sides of the permeable film.

Figure 3:
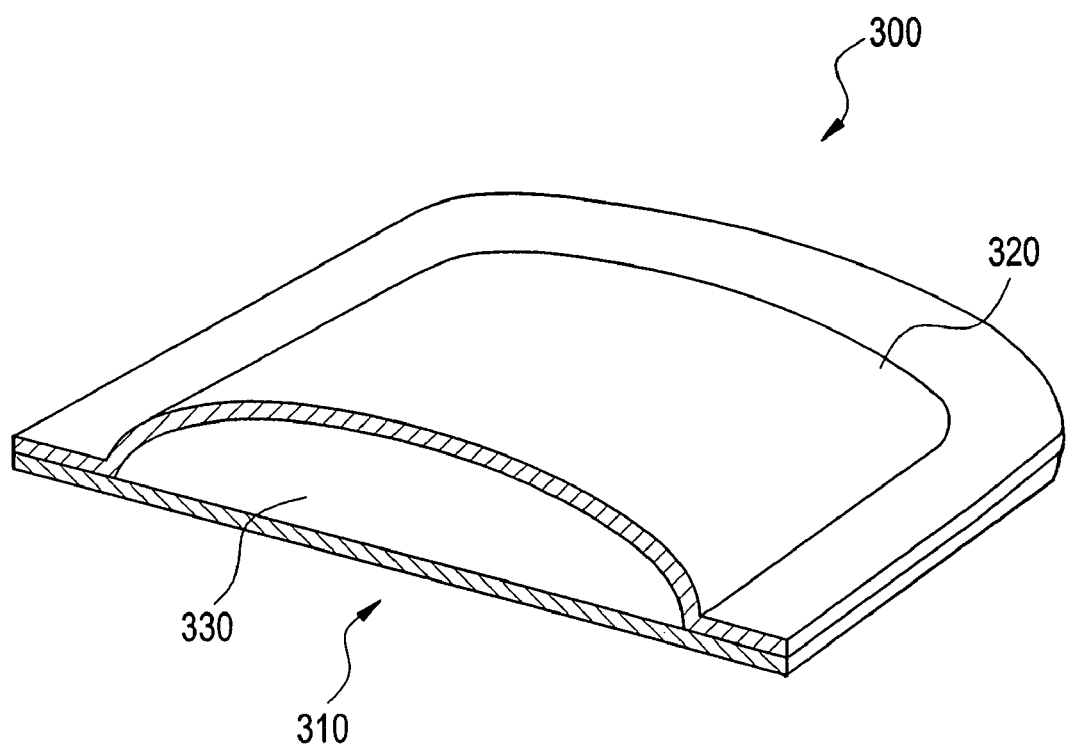
FIG. 3 illustrates one embodiment of a gas emitting pouch system.

FIG. 3 illustrates a gas emitting pouch system 300. The gas emitting pouch system 300 is shown as an exemplary perspective cut-away view to more clearly illustrate the invention. In one embodiment, the gas emitting pouch system 300 is configured to contain a gas that is dispensed to the local area surrounding the gas emitting pouch system 300. For example, the different gases contained within the gas emitting pouch system 300 may include but is not limited to oxygen, carbon dioxide, and/or nitrogen.

The gas emitting pouch system 300 includes a first permeable film 310, a second permeable film 320, and a reservoir 330.

In one embodiment, the first permeable film 310 is coupled with the second permeable film 320 and forms the reservoir 330 for storing gas within the gas emitting pouch system 300. For example, the first and second permeable films 310 and 330 may be constructed of polyurethane, polyethylene, silicone films, polyvinylchloride, and the like.

The reservoir 330 is configured to store a gas while the gas emitting pouch system 300 is being used. In one embodiment, the stored gas within the reservoir 330 is controllably released to the area surrounding the gas emitting pouch system 300 through the first and second permeable films 310 and 320.

The amount and rate of gas released through the gas emitting pouch system 300 may vary according to the concentration gradients of the gas across the permeable films that comprise the walls of reservoir 330 and the materials used as the first and second permeable films 310 and 320. 310 and 320 can be the same or different materials. The amount and rate of release of gas can be different on the opposite sides, this can occur when 310 and 320 have different permeabilities. Other factors such as temperature, humidity and atmospheric pressure may also affect the amount of gas released.

The elements comprising the gas emitting pouch system 300 are shown for illustrative purposes only. Deletion or substitution of any shown elements does not depart from the spirit and scope of the invention. Similarly, the addition of new elements does not depart from the spirit and scope of the invention.

In one embodiment, the gas emitting pouch system 300 is configured prefilled with the desired gas concentrations and is stored within the packaging system 200 (FIG. 2) prior to releasing gas into the surrounding environment, also pre-filled with the same gas concentrations as in the gas emitting pouch, in order to maintain the levels in the pouch. In another embodiment, the gas within the reservoir 330 within the gas emitting pouch system 300 comes to equilibrium within the packaging system 200 so that both the pouch and the package reach the target concentrations.

In one embodiment, the gas emitting pouch system 300 is configured to be placed in an environment where the gas stored within the reservoir 330 is released steadily into the surrounding environment, as the gradient doesn't change appreciably. In another embodiment, the release rate of gas from the reservoir 330 into the surrounding environment slows as the surrounding environment becomes saturated with the gas. Subsequent to the saturation, the gas emitting pouch system 300 acts as a gas reservoir; as gas is dissipated from the surrounding environment, there is a local supply of gas within the reservoir 330 to be provided to the surrounding environment, governed by the transfer rate across the permeable film.

The gas emitting pouch 300 has many applications which may include non-medical applications such as applying the gas emitting pouch 300 to effect environments in containers for any purpose such as lab experiments, food preservation, to accelerate degradation, to prevent corrosion, and the like.

Figure 4:
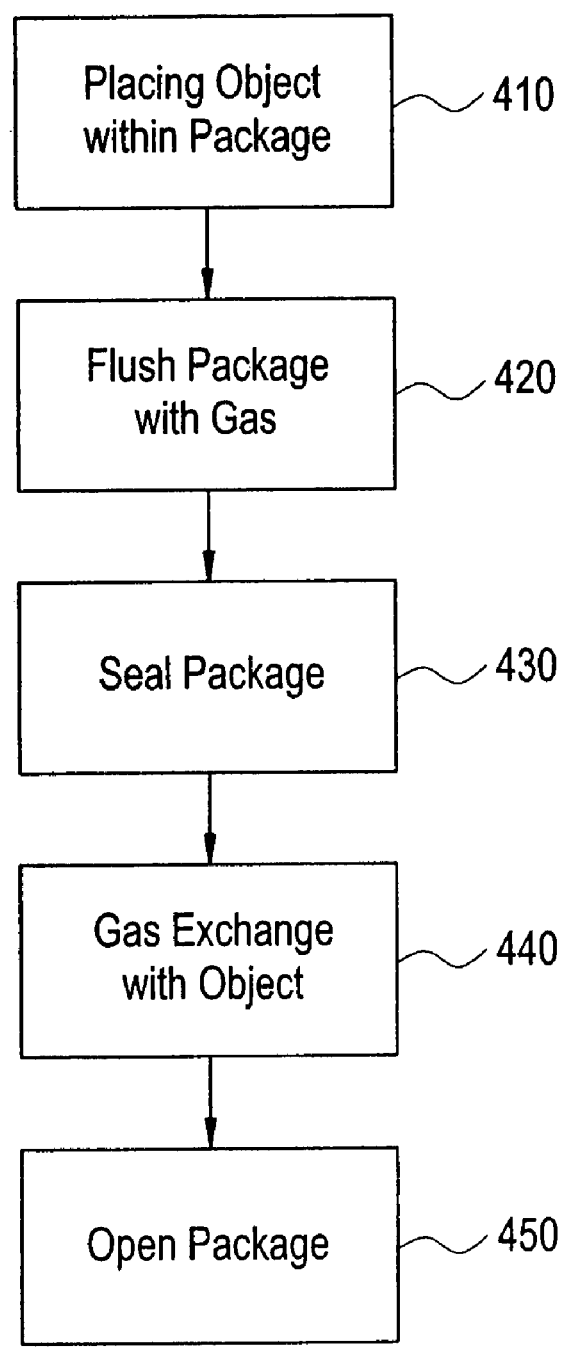
FIG. 4 illustrates a flow diagram for utilizing a packaging system according to one embodiment of the invention.
Figure 5:
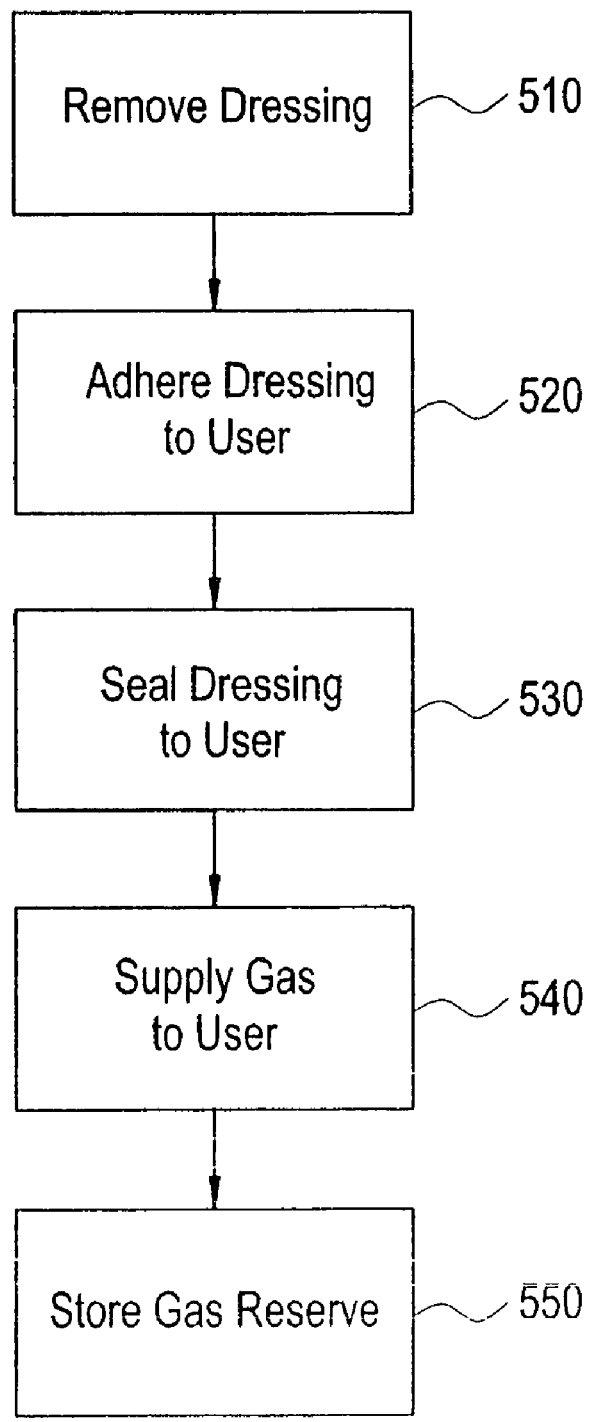
FIG. 5 illustrates a flow diagram for utilizing a dressing system according to one embodiment of the invention.

The flow diagrams as depicted in FIGS. 4, and 5 illustrate merely one embodiment of the invention. The flow diagrams in FIGS. 4 and 5 are one particular use of the invention based on a specific application. In other embodiments, the invention may be utilized with other applications. The blocks within the flow diagrams may be performed in a different sequence without departing from the spirit of the invention. Further, blocks may be deleted, added, or combined within each of the flow diagrams without departing from the spirit of the invention.

The flow diagram in FIG. 4 illustrates an exemplary process of utilizing the packaging system 200 according to one embodiment.

In Block 410, a gas-retaining object is placed within the packaging system 200. In one embodiment, the gas-retaining object is the dressing system 100. In another embodiment, the gas-retaining object is gas emitting pouch system 300. In yet another embodiment, the gas-retaining object may be any item that is configured to retain and controllably release a gas from the object.

In Block 420, the packaging system 200 is flushed with a gas. In one embodiment, the packaging system 200 is flushed with the same gas contained with the gas-retaining object. For example, the dressing system 100 may be pre-filled with oxygen and placed within the packaging system. By flushing the packaging system 200 with oxygen, the packaging system 200 ensures that the dressing system 100 retains the pre-filled oxygen content.

In another embodiment, the packaging system 200 is flushed with a different gas than the gas contained with the gas-retaining object. For example, the dressing system 100 may contain air that contains other gases in addition to oxygen and may be placed within the packaging system 200. By flushing the packaging system 200 with pure oxygen, the packaging system 200 diffuses the dressing system 100 with additional oxygen until the gas within the packaging system 200 and the gas within the dressing system 100 have reached an equilibrium.

In Block 430, the packaging system 200 is sealed after placing the gas-retaining object within the packaging system 200 and flushing the packaging system 200 with a gas.

In Block 440, if the gas within the gas retaining device and the gas within the packaging system 200 differ, then an exchange of gas occurs until an equilibrium is achieved. For example, by using the above example describing a dressing system 100 that contains air which is sealed within the packaging system 200 flushed with pure oxygen, the oxygen diffuses into within the dressing system 100, while nitrogen diffuses out of the dressing system 100 into the package 200 until an equilibrium is achieved between the gas within the dressing system 100 and the packaging system 200. In this embodiment, the gas may be exchanged through the permeable film 160 (FIG. 1).

In Block 550, the packaging system 200 may be opened to remove the gas-retaining object. The packaging system 200 may be utilized to store the gas-retaining object without degrading the gas within the gas-retaining object. In another embodiment, the packaging system 200 may be utilized to infuse the gas-retaining object with a gas.

The flow diagram in FIG. 5 illustrates an exemplary process of utilizing the dressing system 100 according to one embodiment.

In Block 510, the dressing system 100 is removed from a packaging.

In Block 520, the dressing system 100 is adhered to a user. In one embodiment, the dressing system 100 may cover a wound or broken skin of the user. In one embodiment, the dressing system 100 utilizes the adhesive backing 150 to adhere the dressing system 100 to the user.

In Block 530, a seal is formed between the dressing system 100 and the user. In one embodiment, the adhesive backing 150 forms the seal between the dressing system 100 and the user.

In Block 540, gas is supplied from the dressing system 100 to the user. In one embodiment, the permeable film 160 is positioned over the wound or broken skin of the user and allows the gas from the dressing system 100 to be supplied to wound of the user.

In another embodiment, the permeable film 160 may be positioned over intact skin of the user and allows the gas from the dressing system 100 to be supplied to the skin of the user. There are numerous practical applications in supplying oxygen to intact skin such as treating sun or radiation damaged skin, exfoliated skin, dermabraded skin, or providing nourishment to aged skin. There may be a synergistic effect with topical agents as well.

In Block 550, the gas within the reservoir 130 of the dressing system 100 may be stored until additional gas is supplied to the user through the permeable film 160.

Another embodiment of the packaging system comprises any of the packaging systems described herein and further comprises a septum, which as defined herein may be a septum, a valve, Luer lock or any resealable opening, through which one or more gases can be introduced into the packaging system, then resealed to prevent gases from escaping. The packaging system may be charged with the one or more gases in the desired ratio on site (e.g., hospital, doctor's office).

In another embodiment, the adhesive layer may comprise a gel. The gel may have semi-adhesive properties, such that the same dressing system can be removed and replaced repeatedly. Examples of gels that may be used are described in U.S. Pat. Nos. 4,839,345, 5,354,790 and 5,583,114.

The foregoing descriptions of specific embodiments of the invention have been presented for purposes of illustration and description.

They are not intended to be exhaustive or to limit the invention to the precise embodiments disclosed, and naturally many modifications and variations are possible in light of the above teaching. The embodiments were chosen and described in order to explain the principles of the invention and its practical application, to thereby enable others skilled in the art to best utilize the invention and various embodiments with various modifications as are suited to the particular use contemplated.

Figure 6:
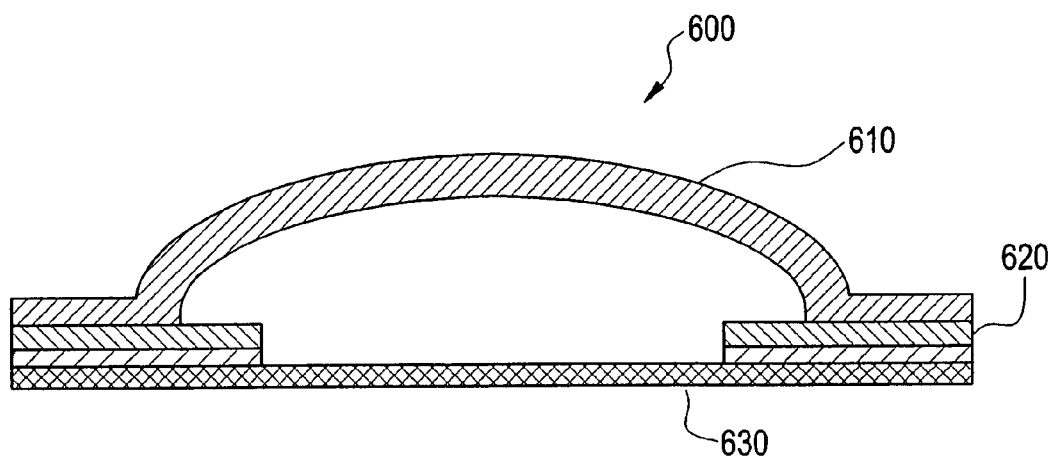
FIG. 6 illustrates one embodiment of a pouch system.

FIG. 6 illustrates a pouch system 600. The pouch system 600 is configured to emit gas into a local environment, similar to the gas emitting pouch system 300. The pouch system 600 includes a first layer 610 and a second layer 630. The first layer 610 and the second layer 630 may be permeable to gases. In one embodiment, the first layer 610 and the second layer 630 are bonded through an intermediate layer 620. The intermediate layer 620 provides the pouch system 600 a more resilient and durable seal between the first layer 610 and the second layer 630 by diverting the load so that more robust shear force is applied to a higher bond strength seal rather than strictly a design that puts all the internal pressure and load on a peel strength surface. By adding the intermediate layer 620 with a narrower diameter than the first layer 610, the seal between the first layer 610 and the second layer 630 is reinforced.

The present invention is useful for wound healing for human and animal patients, for use in laboratories, and anywhere a specific gas or combination of gases is required to reach a specific, discrete site.

The foregoing descriptions of specific embodiments of the invention have been presented for purposes of illustration and description. They are not intended to be exhaustive or to limit the invention to the precise embodiments disclosed, and naturally many modifications and variations are possible in light of the above teaching. The embodiments were chosen and described in order to explain the principles of the invention and its practical application, to thereby enable others skilled in the art to best utilize the invention and various embodiments with various modifications as are suited to the particular use contemplated.

REFERENCES

1. Whitney J D, "Physiological Effects of Tissue Oxygenation on Wound", Heart & Lung, Vol. 18., No. 5, pp. 466–474, September 1989.
2. Gruber R P, et al., "Skin Permeability to Oxygen and Hyperbaric Oxygen", ARCH. SURG., Vol. 101, pp. 69–70, July 1970.
3. Eaglstein W H, "Experiences with Biosynthetic Dressings", J. AmM. Acad. Dermatol., Vol. 12 (2 Pt 2), pp. 434–40, Febuary 1985.
4. Niinikoski J, et al., "Combination of Hyperbaric Oxygen, Surgery, and Antibiotics in the Treatment of Clostridial Gas Gangrene", Infections in Surgery, pp. 23–37, January 1983.
5. Fischer B H, "Treatment of Ulcers on the Legs with Hyperbaric Oxygen", J. Derm. Surg., Vol. 1, No. 3, pp. 55–58, October 1975.
6. Heng M, et al., "A Simplified Hyperbaric Oxygen Technique for Leg Ulcers", Arch Dermatol, Vol. 120, pp. 640–645, May 1984.
7. Olejniczak S, et al., "Topical Oxygen Promotes Healing of Leg Ulcers", Medical Times, Vol. 104, No. 12, pp. 114–121, December 1976.
8. Transcript of United States Food & Drug Administration, Center for Drug Evaluation & Research, Dermatologic and Ophthalmic Drugs Advisory Committee, 46th Meeting, pp. 15–28, Jul. 14, 1997 (http://www.fda.gov/ohrms/dockets/ac/97/transcpt/3308t1.pdf).
9. Zhao L L, Davidson J D, Wee S C, Roth S, Mustoe T A, "Effect of Hyperbaric Oxygen and Growth Factors on Rabbit Ear Ischemic Ulcers," Arch Surg/Vol. 129, October 1994.
10. Winter G D, Perins D J D, Proceedings of the 4th Intl Congress on Hyperbaric Medicine, Igaku Shoin Ltd, p. 363, 1970.
11. Silver I A, in *Wound Healing & Wound Infection*, ed. Hunt T K, Appleton-Century-Crofts, NY, p26, 1980.
12. Prockop D J, et al., "Oxygen-18 studies on the conversion of proline to collagen hydroxyproline", Arch Biochem BioPhys V101, p. 499, 1963.
13. Winter G D., Advances in Exp Med and Bio, V94, p. 673–8, Jul. 4, 1977.
14. Silver I A, in *Epidermal Wound Healing*, ed. Maibach H & Rovee D, Year Book Medical Publishers, Inc, Chicago, p. 291–305, 1972.
15. Kaufman T, et al., Surgical Forum V34, pp. 111–113, 1983.
16. Niinikoski J, Clin Plast. Surg, V4, p. 361, 1977.
17. Kaufman T, et al., Burns, V9, pp. 169–173, 1983.
18. Utkina O T, Biol. Abstr., V45, 6289, 1964.
19. Brody A L, Food Technology, Vol. 55, No. 9, pp. 104–106, Sep. 2001.
20. Hoogenwerf S W, et al., Letters in Applied Microbiology, Vol. 35, Issue 5, p. 419, Nov. 2002.
21. Devlieghere F, et al., "Modified atmosphere packaging: state of the art", http://www.ifis.co.uk/hottopics/MAParticle2.PDF, September 2000.
22. Labell, "Controlled & Modified Atmosphere Packaging", Food Processing, p. 152, January 1985.
23. "Biobased Packaging Materials for the Food Industry", ed. C J Weber, http://www.nf-2000.org/publications/f4046fin.pdf, November 2000.

What is claimed is:

1. A method of charging an apparatus, the apparatus including a top layer and a bottom layer sealed around the perimeter of the layers to form a reservoir between the layers, wherein the top layer has gas barrier properties and the bottom layer has gas transfer properties, the method, comprising:
    placing the apparatus within a substantially gas-impermeable container, wherein the reservoir of the apparatus is pre-filled with one or more first gases according to a first ratio;
    flushing the container with one or more second gases sufficient to produce a second ratio of gases within the container, wherein at least one of the second gases is at a concentration greater than atmospheric; and
    hermetically sealing the container and allowing the second and first gases to permeate into and out of the reservoir of the apparatus via the bottom layer such that the first and second gases in the apparatus and container reach equilibrium to produce a third ratio of gases, wherein at least one of the gases is at a concentration greater than atmospheric.

2. The method according to claim 1, further comprising providing the apparatus.

3. A method of charging an apparatus comprising:
    placing an apparatus within a substantially gas-impermeable container, wherein the apparatus includes a reservoir having a gas-permeable portion and being pre-filled with one or more predetermined first gases according to a first ratio, wherein at least one of the first gases is at a concentration greater than atmospheric;

flushing the container with one or more predetermined second gases sufficient to produce a second ratio of gases within the container; and hermetically sealing the container and allowing the second and first gases to permeate into and out of the reservoir of the apparatus via the gas permeable portion such that the first and second gases in the apparatus and container reach equilibrium to produce a third ratio of gases.

4. The method according to claim 3, further comprising providing the apparatus.

* * * * *